United States Patent [19]

Aschwanden et al.

[11] Patent Number: 5,034,402

[45] Date of Patent: Jul. 23, 1991

[54] METHODS AND PHARMACEUTICAL COMPOSITIONS USING PYRROLIDINE DERIVATIVES

[75] Inventors: Werner Aschwanden, Ettingen; Emilio Kyburz, Reinach, both of Switzerland

[73] Assignee: Hoffmann-La Roche Inc., Nutley, N.J.

[21] Appl. No.: 508,675

[22] Filed: Apr. 12, 1990

Related U.S. Application Data

[60] Continuation of Ser. No. 132,523, Dec. 14, 1987, abandoned, which is a continuation of Ser. No. 937,855, Dec. 4, 1986, abandoned, which is a division of Ser. No. 624,303, Jun. 25, 1984, Pat. No. 4,650,878, which is a division of Ser. No. 506,147, Jun. 20, 1983, Pat. No. 4,476,308, which is a continuation of Ser. No. 397,751, Jul. 13, 1982, abandoned.

[30] Foreign Application Priority Data

Jul. 24, 1981 [CH] Switzerland .................. 4849/81
May 5, 1982 [CH] Switzerland .................. 2768/82

[51] Int. Cl.$^5$ .............. A61K 31/40; A61K 31/445; A61K 31/535
[52] U.S. Cl. ..................... 514/326; 514/252; 514/237.2; 514/422; 514/425
[58] Field of Search ............ 514/425, 422, 326, 252, 514/237.2

[56] References Cited

U.S. PATENT DOCUMENTS

| | | | |
|---|---|---|---|
| 3,459,738 | 8/1969 | Merren | 260/239.3 |
| 4,118,396 | 10/1978 | Pifferi et al. | 548/544 X |
| 4,124,594 | 11/1978 | Mongazzi et al. | 548/544 |
| 4,145,347 | 3/1979 | L'Italien et al. | 544/141 X |
| 4,173,569 | 11/1979 | Banfi et al. | 548/544 |
| 4,341,790 | 7/1982 | Betzig et al. | 546/281 X |
| 4,372,960 | 2/1983 | L'Italien | 546/208 X |
| 4,452,807 | 6/1984 | Aschwanden et al. | 548/110 X |
| 4,476,308 | 10/1984 | Aschwanden et al. | 548/406 X |
| 4,650,878 | 3/1987 | Aschwanden et al. | 548/544 |

FOREIGN PATENT DOCUMENTS

| | | |
|---|---|---|
| 845099 | 2/1977 | Belgium . |
| 864269 | 5/1978 | Belgium . |
| 892942 | 10/1982 | Belgium . |
| 2923975 | 12/1980 | Fed. Rep. of Germany . |
| 2924011 | 12/1980 | Fed. Rep. of Germany . |
| 3104703 | 11/1981 | Fed. Rep. of Germany . |
| 8100579 | 9/1981 | Netherlands . |
| 1309692 | 3/1973 | United Kingdom . |
| 2055835A | 3/1981 | United Kingdom . |

Primary Examiner—Joseph Paul Brust
Attorney, Agent, or Firm—George M. Gould; Bernard S. Leon; William G. Isgro

[57] ABSTRACT

Pyrrolidine derivatives of the formula

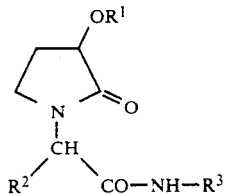

wherein $R^1$ is hydrogen or lower alkanoyl, $R^2$ is hydrogen or lower alkyl and $R^3$ is hydrogen, lower alkyl or a group of the formula $-(CH_2)_n-NR^4R^5$, wherein n is a whole number of 2 to 4 and $R^4$ and $R^5$ each, independently, are hydrogen or lower alkyl, or $R^4$ and $R^5$ taken together with the nitrogen atom are a pyrrolidinyl, piperidinyl, piperazinyl or morpholinyl group which is optionally substituted by one or two lower alkyl groups, enantiomers thereof, and acid addition salts of compounds of formula I and their enantiomers which are basic, are useful in the control or prevention of cerebral insufficiency or in the improvement of intellectual capacity. The compounds of formula I of the invention can be prepared starting from starting materials hereinafter described, and are useful as medicaments, for example, in the form of pharmaceutical preparations.

12 Claims, No Drawings

METHODS AND PHARMACEUTICAL COMPOSITIONS USING PYRROLIDINE DERIVATIVES

This application is a continuation of application Ser. No. 132,523, filed Dec. 14, 1987, now abandoned, which in turn is a continuation of application Ser. No. 937,855 filed Dec. 4, 1986, now abandoned, which is a division of Ser. No. 624,303, filed June 25, 1984, which is now U.S. Pat. No. 4,650,878, which is a division of Ser. No. 506,147, filed June 20, 1983, which is now U.S. Pat. No. 4,476,308, which is a continuation of parent Ser. No. 397,751, filed July 13, 1982, now abandoned.

BRIEF SUMMARY OF THE INVENTION

The invention relates to pyrrolidine derivatives. In particular, it relates to pyrrolidine derivatives of the formula

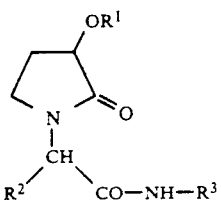

wherein $R^1$ is hydrogen or lower alkanoyl, $R^2$ is hydrogen or lower alkyl and $R^3$ is hydrogen, lower alkyl or a group of the formula $-(CH_2)_n-NR^4R^5$, wherein n is a whole number of 2 to 4 and $R^4$ and $R^5$ each independently are hydrogen or lower alkyl, or $R^4$ and $R^5$ taken together with the nitrogen atom are a pyrrolidinyl, piperidinyl, piperazinyl or morpholinyl group which is optionally substituted by one or two lower alkyl groups, including enantiomers thereof, and pharmaceutically acceptable acid addition salts of the compounds of formula I or enantiomers thereof, which are basic.

DETAILED DESCRIPTION OF THE INVENTION

The invention relates to pyrrolidine derivatives. In particular, it relates to pyrrolidone derivatives of the formula

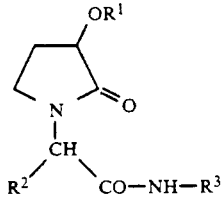

wherein $R^1$ is hydrogen or lower alkanoyl, $R^2$ is hydrogen or lower alkyl and $R^3$ is hydrogen, lower alkyl or a group of the formula $-(CH_2)_n-NR^4R^5$, wherein n is a whole number of 2 to 4, and $R^4$ and $R^5$ each independently are hydrogen or lower alkyl, or $R^4$ and $R^5$ taken together with the nitrogen atom are a pyrrolidinyl, piperidinyl, piperazinyl or morpholinyl group which is optionally substituted by one or two lower alkyl groups, including enantiomers thereof, and pharmaceutically acceptable acid addition salts of the compounds of formula I or enantiomers thereof, which are basic, i.e. where $R^3$ is a group of the formula $-(CH_2)_n-NR^4R^5$.

The compounds of formula I of the invention posses valuable pharmacodynamic properties.

The invention relates to the compounds of formula I and acid addition salts of compounds of formula I which are basic, the preparation of these compounds, intermediates for the preparation of these compounds, medicaments containing these compounds and the preparation of such medicaments as well as the use of compounds of formula I and of acid addition salts of compounds of formula I which are basic in the control or prevention of illnesses or in the improvement of health, especially in the control or prevention of cerebral insufficiency or in the improvement of intellectual capacity.

The term "lower alkyl" as used herein denotes straight-chain or branched-chain saturated hydrocarbon groups which contain at most 7, preferably at most 4, carbon atoms such as methyl, ethyl, n-propyl, isopropyl, n-butyl, isobutyl, s-butyl, t-butyl and the like. The term "lower alkanoyl" denotes straight-chain or branched-chain saturated fatty acid groups which contain at most 8, preferably at most 4, carbon atoms such as formyl, acetyl, propionyl, butyryl, isobutyryl and the like.

The compounds of formula I contain at least one asymmetrically substituted carbon atom; the invention embraces not only the optionally uniform enantiomeric forms of these compounds, but also mixtures thereof (especially the racemates).

In a preferred aspect, the invention embraces compounds of formula I in which $R^1$ and $R^2$ are hydrogen and $R^3$ is hydrogen, 2-(diisopropylamino)ethyl or 2-(2,6-dimethyl-1-piperidinyl)ethyl Particularly preferred compounds of formula I are:
(R/S)-cis-N-[2-(2,6-dimethyl-1-piperidinyl)ethyl]-2-(3-hydroxy-2-oxo-1-pyrrolidinyl) acetamide and
(R/S)-2-(3-hydroxy-2-oxo-1-pyrrolidinyl)acetamide.

Other preferred compounds of formula I are:
(R)-cis-N-[2-(2,6-Dimethyl-1-piperidinyl)ethyl]-2-(3-hydroxy-2-oxo-1-pyrrolidinyl) acetamide,
(S)-cis-n-[2-(2,6-dimethyl-1-piperidinyl)ethyl]-2-(3-hydroxy-2-oxo-1-pyrrolidinyl) acetamide,
(R)-2-(3-hydroxy-2-oxo-1-pyrrolidinyl)acetamide,
(S)-2-(3-hydroxy-2-oxo-1-pyrrolidinyl)acetamide and
(R/S)-N[2-(diisopropylamino)ethyl]-2-(3-hydroxy-2-oxo-1-pyrrolidinyl)acetamide.

The compounds of formula I and, insofar as they are basic, their pharmaceutically acceptable acid addition salts can be prepared in accordance with the invention by (a) reacting a compound of the formula

$$H_2N-R^3 \qquad II$$

wherein $R_3$ is as previously described, with a carboxylic acid of the formula

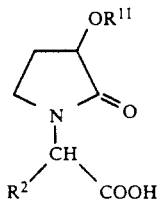

wherein $R^2$ is as previously described and $R^{11}$ is hydrogen or lower alkanoyl or, where $R^3$ in formula III is hydrogen, also another group cleavable by means of ammonia, or with a reactive functional derivative thereof, or (b) acylating a compound of the formula

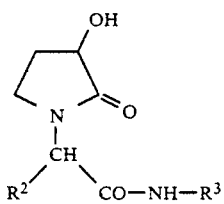

Ib wherein $R^2$ and $R^3$ are as previously described, with an agent yielding a lower alkanoyl group, or (c) cleaving the protecting group denoted by Z from a compound of the formula

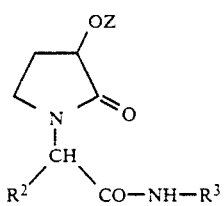

IV wherein $R^2$ and $R^3$ are as previously described, and Z is a protecting group, and (d) if desired, separating an obtained mixture of diastereoisomers into the corresponding racemates, and/or (e) if desired, resolving an obtained racemate of a compound of formula I in which $R^1$ is hydrogen and/or $R^3$ is a basic group into the optical antipodes or enantiomers, and/or (f) if desired, converting a compound of formula I which is basic into a pharmaceutically acceptable acid addition salt.

In accordance with process variant (a), compounds of formula I can be prepared by reacting an amine of formula II with a carboxylic acid of formula III or a reactive functional derivative thereof. If the free carboxylic acid of formula III is used, then the reaction is conveniently carried out in an inert organic solvent and in the presence of a condensation agent. Suitable inert organic solvents are, for example, ethers such as tetrahydrofuran, diethyl ether, t-butyl methyl ether, dioxane, ethylene glycol dimethyl ether or the like, halogenated hydrocarbons such as methylene chloride, chloroform, 1,2-dichloroethane or the like, acetonitrile, dimethylformamide or the like. Suitable condensation agents are, for example, dicyclohexylcarbodiimide, optionally together with N-hydroxysuccinimide, 1-(lower alkyl)-2-halopyridinium salts and the like. In this case, the reaction is carried out at a temperature range of about 0° C. to the boiling point of the reaction mixture, but conveniently at room temperature.

If a reactive functional derivative of a carboxylic acid of formula III is used in the foregoing reaction, then there primarily come into consideration corresponding carboxylic acid esters, especially lower alkyl esters such as the methyl and ethyl ester, corresponding carboxylic acid halides, especially the carboxylic acid chlorides, corresponding carboxylic acid anhydrides and mixed anhydrides, for example, with mesitylenesulfonic acid, ethyl formate and the like, corresponding carboxylic acid imidazolides and the like. The reactive functional derivatives of the carboxylic acids of formula III need not be isolated in every case, but can be prepared in situ and immediately used in the reaction. The reaction is conveniently carried out in an inert organic solvent, with especially the solvents mentioned earlier coming into consideration. Depending on the reactivity of the carboxylic acid derivative used, the reaction is carried out at a temperature range of about 0° C. to the boiling point of the reaction mixture.

If the free carboxylic acid of formula III is used in the presence of a reactive condensation agent or if an especially reactive functional derivative of the free carboxylic acid of formula III is used, for example, the corresponding carboxylic acid halides or anhydrides, then there come into consideration as starting materials only those compounds in which $R^{11}$ is not hydrogen.

In a preferred embodiment, a lower alkyl ester of a carboxylic acid of formula III is used and excess amine of formula II is used as the solvent. If an amide of formula I which is unsubstituted on the nitrogen atom is desired, then the compound of formula II is ammonia, which is preferably used in aqueous or alcoholic, especially methanolic, solution. In this case it is to be observed that when an excess of ammonia is used, a lower alkanoyl group which may be present in the starting material of formula III is cleaved, and there is obtained a compound of formula I in which $R^1$ is hydrogen. This also applies when $R^{11}$ in the starting material of formula III is another group cleavable by means of ammonia. The groups cleavable by means of ammonia are primarily acyl groups, for example alkanoyl groups, such as the lower alkanoyl groups mentioned earlier, alkanoyl groups substituted by halogen, alkoxy groups or aryloxy groups or the like, such as chloroacetyl, trifluoroacetyl, methoxyacetyl, phenoxyacetyl and the like, alkoxycarbonyl or aralkoxycarbonyl groups optionally substituted by halogen or the like such as benzyloxycarbonyl, trichloroethoxycarbonyl, tribromoethoxycarbonyl and the like, aroylcarbonyl groups, such as benzoylformyl, acyl groups of optically active acids such as (3-oxo-4,7,7-trimethyl-2-oxabicyclo[2.2.1]hept-1-yl)carbonyl and the like.

In accordance with process variant (b), compounds of formula I in which $R^1$ is lower alkanoyl can be prepared by treating a compound of formula Ib with an agent yielding a lower alkanoyl group. Suitable agents yielding a lower alkanoyl groups are, for example, lower alkanecarboxylic acid halides, especially the chlorides, corresponding anhydrides and mixed anhydrides, for example, with the acids mentioned earlier, corresponding lower alkanecarboxylic acid imidazolides and the like. This reaction is conveniently carried out in an inert organic solvent, whereby there come into consideration especially ethers such as tetrahydrofuran, diethyl ether, t-butyl methyl ether, dioxane, ethylene glycol dimethyl ether or the like, halogenated hydrocarbons such as methylene chloride, chloroform, 1,2-dichloroethane or the like, aromatic hydrocarbons such as toluene and the like, acetonitrile, dimethylformamide or the like. The reaction temperature conveniently lies in a range of about 0° C. to the boiling point of the reaction mixture.

In accordance with process variant (c), compounds of formula I in which $R^1$ is hydrogen can be prepared by cleaving the protecting group denoted by Z from a compound of formula IV. As protecting groups in the compounds of formula IV there are, of course, suitable only those which can be cleaved by methods which selectively remove these protecting groups without affecting other structural elements present in the molecule. Suitable protecting groups for the present process variant are, for example, readily cleavable metal-organic groups, especially trialkylsilyl groups such as the trimethylsilyl group, the t-butyldimethylsilyl group and the like, readily cleavable acetal and ketal protecting groups such as the tetrahydropyran-2-yl group, the 4-methoxy-tetrahydropyran-4-yl groups and the like, the benzyl group and the like. The removal of the protecting group from the compounds of formula IV is carried out according to known methods, whereby, of course, when choosing the method to be used the nature of the protecting group to be removed must be taken into consideration and it is to be observed that only the protecting group is selectively removed without affecting other structural elements present in the molecule. The trimethysilyl group can be cleaved, for example, by treatment with dilute hydrochloric acid in tetrahydrofuran or by heating in aqueous ethanol or methanol to the boiling temperature. The acetal and ketal protecting groups mentioned earlier can be cleaved under mild acidic aqueous conditions, for example, by means of 0.1N hydrochloric acid or by trans-acetalization with a lower alkanol such as mentioned or ethanol in the presence of an acid catalyst such as hydrochloric acid, pyridinium p-toluenesulfonate, p-toluenesulfonic acid or the like. The benzyl group can be cleaved, for instance, hydrogenolytically, for example, with a catalyst optionally bound to a carrier such as platinum, platinum oxide, palladium or the like.

The separation of an obtained mixture of diastereoisomers into the corresponding racemates is carried out according to known methods and familiar to any person skilled in the art. The desired separation can be carried out, for example, for means of chromatographic methods.

Racemates of compounds of formula I in which $R^1$ is hydrogen and/or $R^3$ is a basic group can be resolved by esterifying these compounds with an optically active carboxylic acid such as tartaric acid, (+)-di-O,O'-p-toluoyl-D-tartaric acid, (−)-(3-oxo-4,7,7-trimethyl-2-oxabicyclo[2.2.1]hept-1-yl)carboxylic acid or the like or by forming a salt with such an acid and subsequently separating the thus obtained diastereoisomeric compounds or salts, for example by fractional crystallization or by means of chromatographic methods, and liberating the optically uniform compounds of formula I by ester cleavage or by treatment with a base.

The preparation of pharmaceutically acceptable acid addition salts of compounds of formula I is carried out according to methods which are generally usual and familiar to any person skilled in the art. There come into consideration not only salts with inorganic acids but also salts with organic acids; for example, hydrochlorides, hydrobromides, sulfates, methanesulfonates, p-toluenesulfonates, oxalates, tartrates, citrates, maleates, ascorbates, acetates and the like.

As mentioned earlier, intermediates for the preparation of the compounds of formula I are also an object of the invention namely the compounds of formulas III and IV hereinbefore insofar as the protecting group is not a lower alkanoyl group.

Lower alkyl esters of the compounds of formula III can be prepared, for example, by treating a pyrrolidinone derivative of the formula

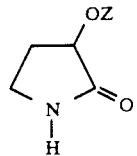

V where Z is as previously described, with a base, for example, sodium hydride, capable of abstracting the hydrogen atom on the nitrogen atom in the 1-position and thereupon reacting the anion obtained with a compound of the formula

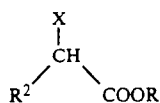

VI wherein $R^2$ is as previously described, X is halogen and R is lower alkyl. There is thus obtained a compound of the formula

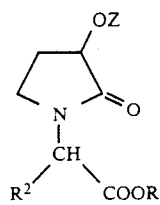

VII wherein $R^2$, R and Z are as previously described. Compounds of formula VII in which Z is lower alkanoyl are lower alkyl esters of compounds of formula III in which $R^{11}$ is lower alkanoyl. Lower alkyl esters of compounds of formula III in which $R^{11}$ is hydrogen can be obtained by cleaving the protecting group denoted by Z from a compound of formula VII.

Carboxylic acids of formula III in which $R^{11}$ is hydrogen, that is, compounds of the formula

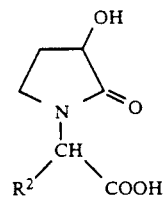

IIIa wherein $R^2$ is as previously described, can be obtained by hydrolyzing the ester group in a composed of formula VII and, previously, subsequently or in the same operation, cleaving the protecting groups denoted by Z. Carboxylic acids of formula III in which $R^{11}$ is lower alkanoyl can be obtained by reacting a compound of formula IIIa with an agent yielding a lower alkanoyl group, for example by treatment with a lower alkanecarboxylic acid anhydride or chloride. Other groups such as (3-oxo-4,7,7-trimethyl-2-oxabicyclo[2.2.1]hept-1-yl)carbonyl can be introduced in an analogous manner, for example, the last-mentioned group can be introduced by means of (3-oxo-4,7,7-trimethyl-2-oxabicyclo[2.2.1]hept-1-yl)carbonyl chloride.

The compounds of formula IV used as starting materials can be obtained by reacting a compound of formula VII with an amine of formula II in analogy to process variant (a). It is to be observed that in this case there come into consideration only those protecting groups which are not affected under these reaction conditions. Especially suitable protecting groups are, for example, the silyl protecting groups mentioned earlier and the benzyl group.

The compounds of formula V can, in turn, be obtained, for example, from 3-hydroxy-2-pyrrolidinone by introducing the desired protecting group; the methods for the introduction of the protecting group vary depending on its nature, but are familiar to any person skilled in the art.

Certain compounds of formula V can also be obtained from 4-amino-2-hydroxybutyric acid using methods which bring about in one operation cyclization and introduction of the desired protecting group. Thus, for example 3-(trimethylsilyloxy)-2-pyrrolidinone can be obtained by reacting 4-amino-2-hydroxybutyric acid in the presence of small amounts of trimethylchlorosilane with hexamethyldisilazane or with bis-(trimethylsilyl)urea or with bis-(trimethylsilyl)acetamide.

The compounds of formulas III and IV contain an asymmetrically substituted carbon atom in the 3-position of the 5-membered heterocycle. The relevant sterochemical relationships determine the stereochemical relationships in the compounds of formula I prepared from the compounds of formulas III and IV. The stereochemical relationships in the 3-position of the 5-membered heterocycle of the compounds of formulas III and IV are, in turn, determined by the intermediates and/or methods used in the preparation of these compounds.

As mentioned earlier, the pyrrolidine derivatives of formula I of the invention, including their enantiomers, are compounds which have extremely valuable pharmacodynamic properties. They exhibit only a slight toxicity and it has been shown that in the animal experiment described hereinafter they are capable of counteracting cerebral insufficiency produced experimentally.

The test apparatus is a "Skinner box" with an electrifiable grid floor (30×40 cm) and a grey plastic platform (15×15×0.8 cm) in the front right corner. Untrained male rats (100-120 g) are placed individually on the platform. As soon as they climb down on to the grid floor they receive an electric foot-shock (0.8 mA). The normal reaction of untrained rats is thereupon to jump back on to the platform. Since, however, the rats still attempt to climb down again, the foot-shock procedure must be repeated three to five times for each animal. After these three to five repetitions per animal, the rats have learned a so-called "passive avoidance response", that is, they no longer attempt to descend to the grid floor, since they know that they are punished when they do so.

Immediately thereafter three groups each comprising 30 animals are set up. The first group receives an injection (i.p.) of 0.3 mg/kg of scopolamine as well as distilled water (2 ml/kg, p.o.). The second group receives an injection (i.p.) of 0.3 mg/kg of scopolamine and an oral dosage of the test substance. The third group receives only distilled water (p.o).

Two (2) hours later each rat is placed once on the platform in the "Skinner box". The criterion for the assessment of this test for the determination of the effect of a preparation on the short-time memory is whether the animal remains or does not remain for 60 seconds on the platform (the result can thus only read "yes" or "no" for each animal). The statistical significance of the difference between the results obtained in the first and in the second groups is determined by means of the Chi-Square Test.

70-75% of the animals treated only with distilled water (p.o.) still remember 2-4 hours after learning the "passive avoidance response" that they should remain on the platform. In the case of 85-92% of the animals treated with scopolamine (0.3 mg/kg i.p.) and distilled water (p.o.) there can be established during 3-4 hours a retrograde effect on the short-time memory, that is, they have forgotten that they must remain on the platform. A substance which is capable of counteracting cerebral insufficiency can reverse the blocking of the short-time memory caused by the injection (i.p.) of 0.3 mg/kg of scopolamine. A dosage of a preparation is denoted as "active" against scopolamine if the number of positive results ("yes") is significantly different from those of control animals treated with scopolamine (0.3 mg/kg i.p.) and only distilled water (p.o.).

In the following Table there are compiled the dosages in which certain compounds of formula I and their enantiomers exhibit a significant activity in the test previously described. Moreover, the Table contains data concerning the acute toxicity ($LD_{50}$ in mg/kg in the case of single oral administration to mice).

TABLE

| Compound | Significant active dosage in mg/kg p.o. | $LD_{50}$ in mg/kg p.o. |
| --- | --- | --- |
| A | 0.01 | >5000 |
|  | 0.03 |  |
|  | 0.1 |  |
|  | 0.3 |  |
|  | 1.0 |  |
| B | 10 | >5000 |
|  | 30 |  |
| C | 10 | >5000 |
|  | 30 |  |
|  | 50 |  |
| D | 10 | >5000 |
|  | 30 |  |
|  | 50 |  |
| E | 3 | >5000 |

Compound A: (R/S)-cis-N-[2-(2,6-Dimethyl-1-piperidinyl)-ethyl]-2-(3-hydroxy-2-oxo-1-pyrrolidinyl)-acetamide.
Compound B: (S)-2-(3-Hydroxy-2-oxo-1-pyrrolidinyl)-acetamide.
Compound C: (R)-2-(3-Hydroxy-2-oxo-1-pyrrolidinyl)-acetamide.
Compound D: (R/S)-2-(3-Hydroxy-2-oxo-1-pyrrolidinyl)-acetamide.
Compound E: (R/S)-N-[2-(Diisopropylamino)ethyl]-2-(3-hydroxy-2-oxo-1-pyrrolidinyl)acetamide.

The compounds of formula I and their enantiomers and pharmaceutically acceptable acid addition salts of those which are basic can be used as medicaments, for example, in the form of pharmaceutical preparations. The pharmaceutical preparations can be administered orally, for example, in the form of tablets, coated tablets, dragees, hard and soft gelatine capsules, solutions, emulsions or suspensions. They can, however, also be administered rectally, for example, in the form of suppositories, or parenterally, for example, in the form of injection solutions.

As mentioned earlier, medicaments containing a compound of formula I, an enantiomer thereof, or a pharmaceutically acceptable acid addition salt of a compound of formula I which is basic also from part of the invention as is a process for the preparation of such medicaments which comprises bringing one or more compounds of formula I, or enantiomers thereof, or pharmaceutically acceptable acid addition salts thereof which are basic and, if desired, one or more other therapeutically valuable substances into a galenical form for administration.

For the preparation of tablets, coated tablets, dragees and hard gelatin capsules, a compound of formula I, an enantiomer or a salt thereof can be processed with pharmaceutical inert, inorganic or organic excipients. Exemplary of such excipients, for example, for tablets, dragees and hard gelatin capsules, are lactose, maize starch or derivatives thereof, talc, stearic acid or its salts and the like.

Suitable excipients for soft gelatin capsules are, for example, vegetable oils, waxes, fats, semi-solid and liquid polyols and the like.

Suitable excipients for the preparation of solutions and syrups are, for example, water, polyols, saccharose, invert sugar, glucose and the like.

Suitable excipients for injectables are, for example, water, alcohols, polyols, glycerin, vegetable oils and the like.

Suitable excipients for suppositories are, for example, natural or hardened oils, waxes, fats, semi-liquid or liquid polyols and the like.

Moreover, the pharmaceutical preparations can contain preservatives, solubilizing agents, stabilizing agents, wetting agents, emulsifying agents, sweetening agents, coloring agents, flavoring agents, salts for the variation of the osmotic pressure, buffers, coating agents or antioxidants. They can also contain other therapeutically valuable substances.

In accordance with the invention, the compounds of formula I, their enantiomers, and pharmaceutically acceptable acid addition salts of those which are basic can be used in the control or prevention of cerebral insufficiency or in the improvement of intellectual capacity; for example, in the case of cerebral seizures, in geriatrics, in alcoholism and the like. The dosage can vary within wide limits and is, of course, fitted to the individual requirements in each particular case. In general, in the case of oral administration a daily dosage of about 10 mg to 2500 mg should be appropriate, although the upper limit quoted can be exceeded when this is shown to be indicated. Qualitatively, the compounds of formula I, their enantiomers and pharmaceutically acceptable acid addition salts of those which are basic have a similar or better action than piracetam, which is known for its therapeutic use.

The Examples which follow further illustrate the invention. All temperatures are given in degrees Centigrade, unless otherwise stated.

EXAMPLE 1

Preparation of (R/S)-2-(3-hydroxy-2-oxo-1-pyrrolidinyl)acetamide (a) 38.3 g of an approximately 55% dispersion of sodium hydride in mineral oil are added portionwise while stirring at a temperature between 45° and 50° within 30 minutes to 51.9 g of (R/S)-3-trimethylsilyloxy-2-pyrrolidinone and 136 ml of ethyl bromoacetate in 520 ml of anhydrous acetonitrile. Thereafter, the mixture is brought to reflux temperature within 30 minutes while stirring, stirred at reflux for an additional 1 hour and then filtered. The filtrate is evaporated and the residue, containing the ethyl (R/S)-2-(3-trimethylsilyloxy-2-oxo-1-pyrrolidinyl)-acetate, is dissolved in 500 ml of tetrahydrofuran. To this solution are added 71 ml of 1N hydrochloric acid and after 15 minutes 7.2 g of sodium hydrogen carbonate, whereupon the mixture is stirred at room temperature for 7 minutes and thereafter evaporated. The residue is extracted three times with acetonitrile and the combined acetonitrile extracts are evaporated. The residue is chromatographed on silica gel (granular size 0.2–0.5 mm). The ethyl (R/S)-2-(3-hydroxy-2-oxo-1-pyrrolidinyl)acetate which is eluted with methylene chloride and ethyl acetate is crystallized from ethyl acetate/n-hexane (1:2) and then has a melting point of 80.5°–81°.

(b) 2.50 g of ethyl (R/S)-2-(3-hydroxy-2-oxo-1-pyrrolidinyl)-acetate are treated with 11.5 ml of approximately 25% ammonium hydroxide solution, whereupon the mixture is stirred at room temperature for 1 hour. The mixture is treated with acetonitrile and evaporated. The residue is treated five times with acetonitrile and in each case again evaporated. There is obtained (R/S)-2-(3-hydroxy-2-oxo-1-pyrrolidinyl)acetamide which melts at 163°–164° after recrystallization from methanol/diethyl ether (1:2).

EXAMPLE 2

Preparation of (R/S)-cis-N-[2-(2,6-dimethyl-1-piperidinyl)ethyl]-2-(3-hydroxy-2-oxo-1-pyrrolidinyl)acetamide 4.5 g of ethyl (R/S)-2-(3-hydroxy-2-oxo-1-pyrrolidinyl)-acetate are heated to 100° for 3.5 hours under nitrogen with 7.1 g of cis-2-(2,6-dimethyl-1-piperidinyl)ethylamine. Thereafter, diethyl ether is added thereto, the mixture is stirred, filtered and the filter residue (6.5 g) is chromatographed on 30 g of silica gel (granular size 0.2–0.5 mm). The (R/S)-cis-N-pi [2-(2,6-dimethyl-1-piperidinyl)-ethyl]-2-(3-hydroxy-2-oxo-1-pyrrolidinyl)acetamide which is eluted with methylene chloride and methanol has a melting point of 131°–132° after recrystallization from ethyl acetate.

EXAMPLE 3

Preparation of (R/S)-N-[2-(diisopropylamino)ethyl]-2-(3-hydroxy-2-oxo-1-pyrrolidinyl)-acetamide 4.5 g of ethyl (R/S)-2-(3-hydroxy-2-oxo-1-pyrrolidinyl)-acetate are heated to 100° under nitrogen for 3.5 hours with 6.1 g of 2-(diisopropylamino)ethylamine. The crude product is chromatographed on aluminum oxide (neutral, activity grade III). With ethyl acetate/ethanol (1:1) and with ethanol there is eluted (R/S)-N-[2-(diisopropylamino)-ethyl]-2-(3-hydroxy-2-oxo-1-pyrrolidinyl)acetamide. After stirring in diethyl ether this has a melting point of 91°–93°; boiling point 230°–250°/0.01 mmHg (bulb-tube).

EXAMPLE 4

Preparation of R-(+)-2-(3-hydroxy-2-oxo-1-pyrrolidinyl)acetamide (a) 89 ml of hexamethyldisilazane and 0.6 ml of trimethylchlorosilane are added to a suspension of 34.0 g of (R)-4-amino-2-hydroxybutyric acid in 340 ml of anhydrous o-xylene. The mixture is heated to boiling for 4 hours while stirring and then evaporated. The residue is extracted four times with toluene. The combined toluene extracts are evaporated in vacuo, whereupon the residue is distilled in three portions. There is obtained (R)-3-(trimethylsilyloxy)-2-pyrrolidinone of boiling point 90°–100°/0.01 mmHg (bulb tube).

(b) The procedure of Example 1, paragraph (a), is repeated with the difference that (R)-3-(trimethylsilyloxy)-2-pyrrolidinone is used as the starting material.

After recrystallization from ethyl acetate/n-hexane, there is obtained ethyl (R)-(+)-2-(3-hydroxy-2-oxo-1-pyrrolidinyl)-acetate of melting point 84°-85°; $[\alpha]_D^{20} = +68°$, $[\alpha]_{546}^{20} = 82°$, $[\alpha]_{365}^{20} = +255°$ (dimethylformamide, c=1.0).

(c) From ethyl (R)-(+)-2(3-hydroxy-2-oxo-1-pyrrolidinyl)-acetate there is obtained according to the process described in paragraph (b) of Example 1 (R)-(+)-2-(3-hydroxy-2-oxo-1-pyrrolidinyl)acetamide which has a melting point of 197°-198°; $[\alpha_D^{20} = +81°$, $[\alpha]_{546}^{20} = +97°$, $[\alpha]_{365}^{20} = +308°$ (dimethylformamide, c=1.0).

EXAMPLE 5

Preparation of (R)-(+)-cis-N-[2-(2,6-dimethyl-1-piperidinyl)ethyl]-2-(3-hydroxy-2-oxo-1-pyrrolidinyl)acetamide From ethyl (R)-(+)-2-(3-hydroxy-2-oxo-1-pyrrolidinyl)-acetate there is obtained according to the process described in Example 2 (R)-(+)-cis-N-[2-(2,6-dimethyl-1-piperidinyl)ethyl]-2-(3-hydroxy-2-oxo-1-pyrrolidinyl)-acetamide which has a melting point of 101°-102°; $[\alpha]_D^{20} = +43°$, $[\alpha]_{546}^{20} = +52°$, $[\alpha]_{365}^{20} = +162°$ (acetonitrile, c=1.00).

EXAMPLE 6

Preparation of (S)-(−)-2-(3-hydroxy-2-oxo-1-pyrrolidinyl)acetamide (a) Analogously to the process in accordance with paragraph (a) of Example 4, from (S)-(−)-4-amino-2-hydroxybutyric acid there is obtained ethyl (S)-(−)-2-(3-hydroxybutyric acid there is obtained ethyl (S)-(−)-2-(3-hydroxy-2oxo-1-pyrrolidinyl)acetate of melting point 85-85.5; $[\alpha]_D^{20} = -69°$; $[\alpha]_{546}^{20} = -84°$, $[\alpha]_{365}^{20} = -259°$ (chloroform, c=1.0).

(b) According to the process described in paragraph (b) of Example 1, from ethyl (S)-(−)-2-(3-hydroxy-1-pyrrolidinyl)-acetate there is obtained (S)-(−)-2-(3-hydroxy-2-oxo-1-pyrrolidinyl)acetamide which has a melting point of 197°-198°; $[\alpha]_D^{20} = -82°$, $[\alpha]_{546}^{20} = -99°$, $[\alpha]_{365}^{20} = -313°$ (dimethylformamide c=1.00).

EXAMPLE 7

Preparation of (S)-(−)-cis-N-[2-(2,6-dimethyl-1-piperidinyl)ethyl]-2-(3-hydroxy-20oxo-1-pyrrolidinyl)acetamide From ethyl (S)-(−)-2-(3-hydroxy-2-oxo-1-pyrrolidinyl)-acetate there is obtained in analogy to the process described in Example 2 (S)-(−)-cis-N-[2-(2,6-dimethyl-1-piperidinyl)ethyl]-2-(3-hydroxy-2-oxo-1-pyrrolidinyl)-acetamide which as a melting point of 101°-103°; $[\alpha]_D^{20} = -44°$, $[\alpha]_{545}^{20} = -53°$, $[\alpha]_{365}^{20} = -165°$ (acetonitrile, c=1.0).

EXAMPLE 8

Preparation of N-methyl-2-(3-hydroxy-2-oxo-1-pyrrolidinyl)acetamide 1.0 g of ethyl (R/S)-2-(3-hydroxy-2-oxo-1-pyrrolidinyl)-acetate is treated with 10 ml of a 40% solution of methylamine in water. After stirring at room temperature for 1 hour, the mixture is evaporated. The residue is shaken five times with acetonitrile in order to remove the water, whereupon in each case it is again evaporated. The residue is treated with diethyl ether. By filtration there is isolated N-methyl-2-(3-hydroxy-2-oxo-1-pyrrolidinyl)-acetamide of melting point 129°-130.5°.

EXAMPLE 9

Preparation of N-[2-(amino)ethyl]-2-(3-hydroxy-2-oxo-1-pyrrolidinyl)acetamide

A mixture of 3.5 g of ethyl (R/S)-2-(3-hydroxy-2-oxo-1-pyrrolidinyl)acetate and 11.2 g of 1,2-ethylenediamine is left to stand at room temperature for 20 hours. The excess 1,2-ethylenediamine is evaporated in vacuo. The residue is dissolved in 40 ml of hot acetonitrile and stirred at room temperature for 2 hours and then in an ice-bath for 1 hour. By filtration there is isolated N-[2-(amino)ethyl]-2-(3-hydroxy-2-oxo-1-pyrrolidinyl)acetamide of melting point 110°-112°.

EXAMPLE 10

Preparation of (R/S)-cis-N-[4-(2,6-dimethyl-1-piperidinyl)butyl]-2-(3-hydroxy-2-oxo-1-pyrrolidinyl)acetamide 3.0 g of ethyl (R/S)-2-(3-hydroxy-2-oxo-1-pyrrolidinyl)acetate and 5.9 g of cis-4-(2,6-dimethyl-1-piperidinyl)butylamine are heated to 95°-100° for 3.5 hours under nitrogen. The mixture is chromatographed on 70 g of aluminum oxide (activity grade III, neutral). The (R/S)-cis-N-[4-(2,6-dimethyl-1-piperidinyl)butyl]-2-(3-hydroxy-2-oxo-1-pyrrolidinyl)acetamide which is eluted with ethanol has a melting point of 90°-92° after crystallization from diethyl ether.

EXAMPLE 11

Preparation of (R/S)-N-[2-(1-piperidinyl)ethyl]-2-(3-hydroxy-2-oxo-1-pyrrolidinyl)acetamide 3.0 g of ethyl (R/S)-2-(3-hydroxy-2-oxo-1-pyrrolidinyl)acetate and 2.87 g of N-(2-aminoethyl)piperidine are heated to 100° for 4 hours under nitrogen. The excess N-(2-aminoethyl)piperidine is distilled in a high vacuum. The (R/S)-N-[2-(1-piperidinyl)ethyl]-2-(3-hydroxy-2-oxo-1-pyrrolidinyl)acetamide remaining as the residue has a melting point of 110°-111° after crystallization from ethyl acetate.

EXAMPLE 12

Preparation of (R/S)-N-[3-(1-morpholinyl)propyl]-2-(3-hydroxy-2-oxo-1-pyrrolidinyl)acetamide 4.0 g of ethyl (R/S)-2-(3-hydroxy-2-oxo-1-pyrrolidinyl)acetate and 6.1 g of N-(3-aminopropyl)morpholine are heated at 95°-100° for 3.5 hours under nitrogen. The mixture is chromatographed on 50 g of silica gel (granular size 0.2-0.5 mm). The (R/S)-N-[3-(1-morpholinyl)propyl]-2-(3-hydroxy-2-oxo-1-pyrrolidinyl)acetamide which is eluted with ethanol has a melting point of 94°-96° after recrystallization from ethyl acetate.

EXAMPLE 13

Preparation of (R/S)-N-[2-(diethylamino)ethyl]-2-(3-hydroxy-2-oxo-1-pyrrolidinyl)acetamide 3.0 g of ethyl (R/S)-2-(3-hydroxy-2-oxo-1-pyrrolidinyl)acetate and 3.7 g of 2-(diethylamino)ethylamine are heated to 95°-100° for 3.5 hours under nitrogen. The mixture is chromatographed on 45 g of aluminum oxide (neutral, activity grade III). The crude (R/S)-N-[2-(diethylamino)ethyl]-2-(3-hydroxy-2-oxo-1-pyrrolidinyl)acetamide which is eluted with methylene chloride and ethyl acetate is again chromatographed on 25 g of aluminum oxide (neutral, activity grade III). The product which is eluted with ethyl acetate and ethanol is distilled in a bulb-tube at about 250°/0.03 mmHg.

EXAMPLE 14

Preparation of
(R/S)-cis-N-[2-(2,6-dimethyl-1-piperidinyl)ethyl]-2-(3-hydroxy-2-oxo-1-pyrrolidinyl)acetamide (a) 15.0 g of ethyl (R/S)-2-(3-hydroxy-2-oxo-1-pyrrolidinyl)acetate are dissolved in 150 ml of absolute alcohol and treated with 1.95 g of sodium dissolved in 38 ml of absolute alcohol. 1.5 ml of ion-free water are added thereto, whereupon the mixture is stirred at room temperature overnight. 250 ml of diethyl ether are added to the resulting suspension and the mixture is then filtered. There is obtained the sodium salt of (R/S)-2-(3-hydroxy-2-oxo-1-pyrrolidinyl)acetic acid. The salt is stirred at room temperature overnight in 200 ml of acetonitrile and 12 ml of 25% hydrochloric acid. The mixture is thereupon evaporated. The evaporation residue is treated twice with acetonitrile and in each case again evaporated. The residue is boiled at reflux in 320 ml of acetonitrile, whereupon it is filtered while hot and the filtrate is stirred in an ice-bath for 3 hours. By filtration there is isolated (R/S)-2-(3-hydroxy-2-oxo-1-pyrrolidinyl)acetic acid of melting point 153°-154°.

(b) 1.30 g of dicyclohexylcarbodiimide dissolved in 6 ml of dimethylformamide are added dropwise at 0° to 1.0 g of (R/S)-2-(3-hydroxy-2-oxo-1-pyrrolidinyl)acetic acid and 1.03 g of 94.7% cis-2-(2,6-dimethyl-1-piperidinyl)ethylamine dissolved in 20 ml of dimethylformamide. The mixture is left to stirred at room temperature for 4 days, treated with 0.23 of ion-free water and evaporated in a water-jet vacuum. The residue is treated five times with toluene and is each case again evaporated. The constituents of the residue which are soluble in chloroform are chromatographed on 60 g of aluminum oxide (activity grade III, neutral). The alcohol eluate is again chromatographed on 15 g of aluminum oxide (activity grade III, neutral). The fractions which are eluted with acetonitrile and ethanol contain, according to the gas chromatogram and mass spectrum, (R/S)-cis-N-[2-(2,6-dimethyl-1-piperidinyl)ethyl]-2-(3-hydroxy-2-oxo-1-pyrrolidinyl)acetamide.

EXAMPLE 15

Preparation of
(R/S)-cis-N-[2-(2,6-dimethyl-1-piperidinyl)ethyl]-2-(3-acetoxy-2-oxo-1-pyrrolidinyl)acetamide (a) 4.0 g of (R/S)-2-(3-hydroxy-2-oxo-1-pyrrolidinyl)acetic acid, 80 ml of absolute tetrahydrofuran and 5 ml of acetyl chloride are boiled at reflux for 4 hours while stirring. Thereafter, the mixture is evaporated. The residue is filtered through silica gel (granular size 0.2-0.5 mm). The evaporation residue of the fractions which are eluted with ethyl acetate is stirred in diethyl ether. By filtration there is isolated (R/S)-2-(3-acetoxy-2-oxo-1-pyrrolidinyl)acetic acid of melting point 95°-96°.

(b) 1.81 g of 2-chloro-1-methyl-pyridinium iodide are suspended in 10 ml of methylene chloride and thereto there are added at room temperature 1.20 g of (R/S)-2-(3-acetoxy-2-oxo-1-pyrrolidinyl)acetic acid. Within 15 minutes there is added dropwise at 0° a solution of 0.98 g of 94.7% cis-2-(2,6-dimethyl-1-piperidinyl)ethylamine and 3.02 ml of triethylamine in 20 ml of methylene chloride, whereupon the mixture is stirred at room temperature for 18 hours. Thereupon, the mixture is evaporated and the residue is chromatographed on aluminum oxide (activity grade III, neutral). The material which is eluted with chloroform is chromatographed on silica gel (granular size 0.2-0.5 mm). The (R/S)-cis-N-[2-(2,6-dimethyl-1-piperidinyl)ethyl]-2-(3-acetoxy-2-oxo-1-pyrroldinyl)acetamide which is eluted with alcohol has a melting point of 120°-122° after crystallization from diethyl ether.

EXAMPLE 16

Preparation of
(R/S)-cis-N-[2-(2,6-dimethyl-1-piperidinyl)ethyl]-1-(3-acetoxy-2-oxo-1-pyrrolidinyl)acetamide 1.0 g of (R/S)-2-(3-acetoxy-2-oxo-1-pyrrolidinyl)acetic acid is placed in 15 ml of absolute tetrahydrofuran, whereupon 0.89 g of N,N'-carbonyldiimidazole is added in one portion. The mixture is stirred at room temperature until the gas evolution is complete. Thereafter, 0.86 g of 94.7% cis-2-(2,6-dimethyl-1-piperidinyl)ethylamine is added and the mixture is left to stand overnight at room temperature and then evaporated. The residue is chromatographed on 60 g of aluminum oxide (activity grade III, neutral). The (R/S)-cis-N-[2-(2,6-dimethyl-1-piperidinyl)ethyl]-2-(3-acetoxy-2-oxo-1-pyrrolidinyl)acetamide which is eluted with methylene chloride has a melting point of 121°-122° after trituration with diethyl ether.

EXAMPLE 17

Preparation of
(R/S)-2-(3-hydroxy-2-oxo-1-pyrrolidinyl)acetamide (a) 1.70 g of ethyl (R/S)-2-(3-hydroxy-2-oxo-1-pyrrolidinyl)acetate are boiled at reflux for 2.5 hours while stirring in 30 ml of methylene chloride and 0.53 ml of acetyl chloride. The mixture is then evaporated. The residue is distilled in a bulb-tube. There is obtained ethyl (R/S)-2-(3-acetoxy-2-oxo-1-pyrrolidinyl)acetate of boiling point 225°/0.01 mmHg.

(b) 0.40 g of ethyl (R/S)-2-(3-acetoxy-2-oxo-1-pyrrolidinyl)acetate is treated with 45 ml of a saturated solution of ammonia in methanol. The mixture is left to stand at room temperature for 1 hour and then evaporated. The residue is treated four times with acetonitrile and in each case again evaporated. There is obtained (R/S)-2-(3-hydroxy-2-oxo-1-pyrrolidinyl)acetamide which melts at 163°-164° after recrystallization from methanol/diethyl ether (1:3).

EXAMPLE 18

Preparation of
(R/S)-2-(3-hydroxy-2-oxo-1-pyrrolidinyl)acetamide 1.0 g of (R/S)-2-(3-acetoxy-2-oxo-1-pyrrolidinyl)acetic acid is boiled at reflux for 2 hours in 20 ml of toluene and 0.54 ml of thionyl chloride. After evaporation of the mixture, the residue is shaken twice with toluene and in each case the toluene is evaporated in vacuo. 0.5 g of the residue, containing crude (R/S)-2-(3-acetoxy-2-oxo-1-pyrrolidinyl)acetic acid chloride, is left to stand overnight in a saturated solution of ammonia in methanol. After evaporation of the solvent, the residue is chromatographed on 5 g of silica gel (granular size 0.2-0.5 mm). (R/S)-2-(3-hydroxy-2-oxo-1-pyrrolidinyl-

EXAMPLE 19

Preparation of
(R/S)-2-(3-hydroxy-2-oxo-1-pyrrolidinyl)acetamide 1.64 g of dicyclohexylcarbondiimide dissolved in 20 ml of chloroform are added at room temperature to 1.5 g of (R/S)-2-(3-acetoxy-2-oxo-1-pyrrolidinyl)acetic acid, 40 ml of chloroform and 0.86 g of N-hydroxysuccinimide. After 4 hours, the solid is filtered, whereupon the filtrate is concentrated and again filtered. The filtrate is evaporated. The residue is treated at room temperature with 40 ml of a saturated solution of ammonia in methanol. The mixture is stirred at room temperature for 5 minutes, 10 ml of ion-free water are then added thereto and the mixture is stirred at room temperature for an additional minutes. The precipitated solid is filtererd. The filtrate is evaporated, the residue is stirred in 30 ml of acetonitrile and the crystallized-out product is recrystallized two more times from acetonitrile. There is obtained (R/S)-2-(3-hydroxy-2-oxo-1-pyrrolidinyl)acetamide of melting point 162°–164°.

EXAMPLE 20

Preparation of
(R/S)-cis-N-[2-(2,6-dimethyl-1-piperidinyl)ethyl]-2-(3-hydroxy-2-oxo-1-pyrrolidinyl)acetamide 1.50 g of (R/S)-2-(3-hydroxy-2-oxo-1-pyrrolidinyl)acetic acid are dissolved in 50 ml of chloroform and 10 ml of dimethylformamide. 1.08 g of N-hydroxysuccinimide are added thereto. Thereafter, 2.08 g of dicyclohexylcarbodiimide dissolved in 25 ml of chloroform are added. The mixture is stirred at room temperature for 4 hours and then precipitated solid is filtered. The filtrate is concentrated to a volume of about 20 ml and the again filtered. The filtrate is evaporated and the residue is treated with 1.70 g of 94.7% cis-2-(2,6-dimethyl-1-piperidinyl)ethylamine. The mixture is left to stand at room temperature overnight and the excess cis-2-(2,6-dimethyl-1-piperidinyl)ethylamine is removed in vacuo. The residue is chromatographed on 60 g of aluminum oxide (activity grade I, basic). The fractions which are eluted with chloroform and alcohol are evaporated. The residue is stirred at room temperature in 35 ml of diethyl ether/ethyl acetate (2:1). There is obtained (R/S)-cis-N-[2-(2,6-dimethyl-1-piperidinyl)ethyl]-2-(3-hydroxy-2-oxo-1-pyrrolidinyl)acetamide (melting point 116°–120°) which melts at 126°–128° after repeated chromatography on aluminum oxide (activity grade III, neutral) and recrystallization from ethyl acetate.

EXAMPLE 21

Preparation of
(R/S)-cis-N-[2-(2,6-dimethyl-1-piperidinyl)ethyl]-2-(3-hydroxy-2-oxo-1-pyrrolidinyl)acetamide 1.2 ml of ethyl chloroformate are placed in 12 ml of chloroform, whereupon there are added dropwise at −30° within 30 minutes 2.0 g of (R/R)-2-(3-hydroxy-2-oxo-1-pyrrolidinyl)acetic acid and 1.74 ml of triethylamine dissolved in 50 ml of chloroform. After stirring at a temperature between −2° and −10° for 12 minutes, 2.07 g of 94.7% cis-2-(2,6-dimethyl-1-piperidinyl)ethylamie dissolved in 10 ml of chloroform are added dropwise. The mixture is left to stand at room temperature overnight. Thereupon, the mixture is evaporated and the residue (6 g) is chromatographed on 120 g of aluminum oxide (activity grade III, neutral). The (R/S)-cis-N-[2-(2,6-dimethyl-1-piperidinyl)ethyl]-2-(3-hydroxy-2-oxo-1-pyrroldinyl)acetamide which is eluted with acetonitrile and ethanol has a melting point of 128°–130° after repeated chromatography on aluminum oxide and recrystallization from ethyl acetate.

EXAMPLE 22

Preparation of
(R/S)-2-(3-hydroxy-2-oxo-1-pyrrolidinyl)acetamide

Analogously to the process of Example 21, from 2 g (R/S)-2-(3-acetoxy-2-oxo-1-pyrrolidinyl)acetic acid using methanolic ammonia in place of cis-2-(2,6-dimethyl-1-piperidinyl)ethylamine there is obtained (R/S)-2-(3-hydroxy-2-oxo-1-pyrrolidinyl)acetamide. The purification is not carried out by chromatography, but by trituration in chloroform. There is obtained a product of melting point 161°–163°.

EXAMPLE 23

Preparation of
(R/S)-cis-N-[2-(2,6-dimethyl-1-piperidinyl)ethyl]-2-(3-acetoxy-2-oxo-1-pyrrolidinyl)acetamide Analogously to the process of Example 21, from 0.8 g (R/S)-2-(3-acetoxy-2-oxo-1-pyrrolidinyl)acetic acid there is obtained a crude mixture. This mixture is chromatographed on 40 g of aluminum oxide (activity grade III, neutral). The (R/S)-cis-N-[2-(2,6-dimethyl-1-piperidinyl)ethyl]-2-(3-acetoxy-2-oxo-1-pyrrolidinyl)acetamide which is eluted with chloroform has a melting point of 121°–122° after trituration is diethyl ether.

EXAMPLE 24

Preparation of
(R/S)-N-[2-(1-pyrrolidinyl)ethyl]-2-(3-hydroxy-2-oxo-1-pyrrolidinyl)acetamide Analogously to the process of Example 21, from N-(2-aminoethyl)pyrrolidine and (R/S)-2-(3-hydroxy-2-oxo-1-pyrrolidinyl)acetic acid there is obtained (R/S)-N-[2-(1-pyrrolidinyl)ethyl]-2-(3-hydroxy-2-oxo-1-pyrrolidinyl)acetamide. The microanalysis shows the following values:

Empirical formula $C_{12}H_{21}O_3N_3$; m.w. 255.32. Calc.: C 56.45%; H 8.29%; N: 16.46%. Found: C 56.11%; H 8.29%; N: 16.32%.

EXAMPLE 25

Preparation of
(R/S)-2-(3-hydroxy-2-oxo-1-pyrrolidinyl)propionamide (a) From (R/S)-3-trimethylsilyloxy-2-pyrrolidinone and ethyl 2-bromopropionate there is obtained according to the process described in paragraph (a) of Example 1 ethyl (R/S)-2-(3-hydroxy-2-oxo-1-pyrrolidinyl)propionate of boiling point 200°/0.05 mmHg (bulb-tube).

(b) According to the process described in paragraph (b) of Example 1, from ethyl (R/S)-2-(3-hydroxy-2-oxo-1-pyrroldinyl)propionate there is obtained, after chromatographic filtration of silica gel (granular size 0.2–0.5 mm), elution with acetonitrile/ethanol (1:1) and crystallization from acetonitrile, (R/S)-2-(3-hydroxy-2-oxo-1-pyrrolidinyl)propionamide of melting point 139°–141°.

EXAMPLE 26

Preparation of
(R/S)-cis-N-[2-(2,6-dimethyl-1-piperidinyl)ethyl]-2-(3-hydroxy-2-oxo-1-pyrrolidinyl)propionamide 1.5 g of ethyl (R/S)-2-(3-hydroxy-2-oxo-1-pyrrolidinyl)propionate are left to stand at room temperature for 24 hours with 2.45 g of cis-2-(2,6-dimethyl-1-piperidinyl)ethylamine. Thereafter, the excess cis-2-(2,6-dimethyl-1-piperidinyl)ethylamine is distilled off in a high vacuum and the residue (3.5 g) is chromatographed on 30 g of silica gel (granular size 0.2–0.5 mm). The (R/S)-cis-N-[2-(2,6-dimethyl-1-piperidinyl)ethyl]-2-(3-hydroxy-2-oxo-1-pyrrolidinyl)propionamide which is eluted with methanol has a melting point of 129°–130° after recrystallization from ethyl acetate.

EXAMPLE 27

Preparation of
(R/S)-cis-N-[2-(2,6-dimethyl-1-piperidinyl)ethyl]-2-(3-hydroxy-2-oxo-1-pyrrolidinyl)butyramide (a) From (R/S)-3-trimethylsilyloxy-2-pyrrolidinone and ethyl 2-bromobutyrate there is obtained according to the process described in paragraph (a) of Example 1 ethyl (R/S)-2-(3-hydroxy-2-oxo-1-pyrrolidinyl)butyrate of boiling point 205°/0.02 mmHg (bulb-tube).

(b) From 2.05 g of ethyl (R/S)-2-(3-hydroxy-2-oxo-1-pyrrolidinyl)butyrate there is obtained according to the process described in Example 2, after chromatographic purification, non-crystallizing (R/S)-cis-N-[2-(2,6-dimethyl-1-piperidinyl)ethyl]-2-(3-hydroxy-2-oxo-1-pyrrolidinyl)butyramide.

EXAMPLE 28

Preparation of
(R/S)-2-(3-hydroxy-2-oxo-1-pyrrolidinyl)butyramide

Analogously to the process in accordance with paragraph (b) of Example 1, from ethyl (R/S)-2-(3-hydroxy-2-oxo-1-pyrrolidinyl)butyrate with 25% ammonium hydroxide solution and recrystallization from acetonitrile there is obtained (R/S)-2-(3-hydroxy-2-oxo-1-pyrrolidinyl)butyramide of melting point 121°–122°.

EXAMPLE 29

Preparation of
(R)-(+)-2-(3-hydroxy-2-oxo-1-pyrrolidinyl)acetamide (a) 2.0 g of ethyl (R/S)-2-(3-hydroxy-2-oxo-1-pyrrolidinyl)acetate are dissolved in 40 ml of pyridine, whereupon there are added portionwise at 0° to +5° 3.54 g of (−)-(3-oxo-4,7,7-trimethyl-2-oxabicyclo[2.2.1]hept-1-yl)carbonyl chloride [[$\alpha$]$_{546}^{20}$=−23°; chloroform, c=2.0]. After stirring at room temperature overnight, the mixture is evaporated. The residue is treated four times with toluene and in each case again evaporated. The residue is chromatographed on 80 g of aluminum oxide (activity grade III, neutral). The fractions which are eluted with chloroform are evaporated and the residue is crystallized in diethyl ether. There is obtained the diastereoisomeric mixture of ethyl 2-/3-[(3-oxo-4,7,7-trimethyl-2-oxabicyclo[2.2.1]hept-1-yl)carbonyloxy]-2-oxo-1-pyrrolidinyl/acetate of melting point 89°–91°.

(b) The separation of the two components can be achieved by high-pressure liquid chromatography of the diastereoisomeric mixture of ethyl 2-/3-[(3-oxo-4,7,7-trimethyl-2-oxabicyclo[2.2.1]hept-1-yl)carbonyloxy]-2-oxo-1-pyrrolidinyl/acetate on commercially obtainable pre-packed Hibar-Lichrosorb RT DIOL columns (250×4 mm, granular size 10 μm) while eluting with 12% tetrahydrofuran and 0.2% isopropylamine in n-hexane.

The melting point of ethyl (R)-2/3-[(3-oxo-4,7,7-trimethyl-2-oxabicyclo[2.2.1]hept-1-yl)carbonyloxy]-2-oxo-1-pyrrolidinyl/acetate is 107°–108° after crystallization from benzene/n-hexane (1:2).

(c) 0.60 g of ethyl (R)-2-/3-[(3-oxo-4,7,7-trimethyl-2-oxabicyclo[2.2.1]hept-1-yl)carbonyloxy]-2-oxo-1-pyrrolidinyl/acetate is stirred at room temperature for 2 hours in 25 ml of a saturated solution of ammonia in methanol. The mixture is evaporated. The residue is treated four times with acetonitrile and in each case again evaporated. By two-fold trituration of the residue in ethyl acetate there is obtained (R)-(+)-2-(3-hydroxy-2-oxo-1-pyrrolidinyl)acetamide of melting point 195°–196°. [$\alpha$]$_D^{20}$=+78°, [$\alpha$]$_{546}^{20}$=+94°, [$\alpha$]$_{365}^{20}$=+302° (dimethylformamide, c=1.0).

EXAMPLE 30

Preparation of
(R/S)-2-(3-acetoxy-2-oxo-1-pyrrolidinyl)acetamide 1.5 g of (R/S)-2-(3-hydroxy-2-oxo-1-pyrrolidinyl)acetamide are heated to reflux for 20 minutes with 13.5 ml of acetyl chloride and 25 ml of chloroform. The mixture is evaporated. The residue is treated four times with toluene and in each case again evaporated. There is obtained (R/S)-2-(3-acetoxy-2-oxo-1-pyrrolidinyl)acetamide which melts at 116°–117° after crystallization from diethyl ether.

EXAMPLE 31

Preparation of
(R/S)-cis-N-[2-(2,6-dimethyl-1-piperidinyl)ethyl]-2-(3-acetoxy-2-oxo-1-pyrrolidinyl)acetamide 2.0 g of (R/S)-cis-N-[2-(2,6-dimethyl-1-piperidinyl)ethyl]-2-(3-hydroxy-2-oxo-1-pyrrolidinyl)acetamide are heated to reflux for 3 hours in 60 ml of chloroform and 1.5 ml of acetyl chloride. After evaporation of the volatile constituents, the residue is treated three times with toluene and in each case again evaporated in vacuo. The residue is chromatographed over aluminum oxide (activity grade III, neutral). The (R/S)-cis-N-[2-(2,6-dimethyl-1-piperidinyl)ethyl]-2-(3-acetoxy-2-oxo-1-pyrrolidinyl)acetamide which is extracted with chloroform has a melting point of 121°–122° after recrystallization from diethyl ether.

EXAMPLE 32

Preparation of
(R/S)-cis-N-[2-(2,6-dimethyl-1-piperidinyl)ethyl]-2-(3-acetoxy-2-oxo-1-pyrrolidinyl)acetamide 0.594 g of (R/S)-cis-N-[2-(2,6-dimethyl-1-piperidinyl)ethyl]-2-(3-hydroxy-2-oxo-1-pyrrolidinyl)acetamide is boiled at reflux for 4 hours with 0.222 g of N-acetylimidazole in 10 ml of toluene. The mixture is chromatographed over 21 g of aluminum oxide (activity grade III, neutral). The (R/S)-cis-N-[2-(2,6-dimethyl-1-piperidinyl)ethyl]-2-(3-acetoxy-2-oxo-1-pyrrolidinyl)acetamide which is eluted with methylene chloride has a melting point of 120°–121° after crystallization from diethyl ether.

EXAMPLE 33

Preparation of (R/S)-2-(3-hydroxy-2-oxo-1-pyrrolidinyl)acetamide

Ethyl of (R/S)-2-(3-trimethylsilyloxy-2-oxo-1-pyrrolidinyl)acetate is obtained analogously to the process in accordance with paragraph (a) of Example 1. After treatment with 25% ammonium hydroxide solution and acidic hydrolysis of the (R/S)-2-(3-trimethylsilyloxy-2-oxo-1-pyrrolidinyl)acetamide, there is obtained crude (R/S)-2-(3-hydroxy-2-oxo-1-pyrrolidinyl)acetamide. After chromatography on silica gel (granular size 0.2–0.5 mm) and elution with acetonitrile/methanol (1:1) (R/S)-2-(3-hydroxy-2-oxo-1-pyrrolidinyl)acetamide in about 80–90% purity can be detected.

EXAMPLE 34

Preparation of (R/S)-cis-N-[2-(2,6-dimethyl-1-piperidinyl)ethyl]-2-(3-hydroxy-2-oxo-1-pyrrolidinyl)acetamide 0.3 g of (R/S)-cis-N-[2-(2,6-dimethyl-1-piperidinyl)ethyl]-2-(3-acetoxy-2-oxo-1-pyrrolidinyl)acetamide is stirred at room temperature for 2 hours in 30 ml of a saturated solution of ammonia in methanol. After evaporation of the methanol, the residue is treated three times with toluene and in each case again evaporated. After trituration in diethyl ether, there is obtained (R/S)-cis-N-[2(2,6-dimethyl-1-piperidinyl)ethyl]-2-(3-hydroxy-2-oxo-1-pyrrolidinyl)acetamide of melting point 129°–130°.

EXAMPLE 35

Preparation of (S) and (R)-cis-N-[2-(2,6-dimethyl-1-piperidinyl)ethyl]-2-(3-hydroxy-2-oxo-1-pyrrolidinyl)acetamide (a) 0.86 g of (−-(3-oxo-4,7,7-trimethyl-2-oxabicyclo[2.2.1]hept-1-yl)carbonyl chloride [[$\alpha$]$_{546}^{20}$ = −23°; chloroform, c=2.0] is added portionwise at 0° to +5° to 1.0 g of (R/S)-cis-N-[2-(2,6-dimethyl-1-piperidinyl)ethyl]-2-(3-hydroxy-2-oxo-1-pyrrolidinyl)acetamide dissolved in 10 ml of pyridine. After stirring at room temperature for 4 hours, the pyridine is evaporated. The residue is treated three times with toluene and in each case again evaporated. The residue is chromatographed on 30 g of aluminum oxide (activity grade III, neutral). The chloroform eluate contains the diastereoisomer mixture of cis-N-(2-[2,6-dimethyl-1-piperidinyl)ethyl]-2-/3-[(3-oxo-4,7,7-trimethyl-2-oxabicyclo[2.2.1]hept-1-yl)carbonyloxy]-2-oxo-1-pyrrolidinyl/acetamide. This substance is further processed without additional purification.

(b) The separation of the two components can be carried out by high-pressure liquid chromatogrpahy of the diastereoisomer mixture of cis-N-[2-(2,6-dimethyl-1-piperidinyl)ethyl]-2-/3-[(3-oxo-4,7,7-trimethyl-2-oxabicyclo[2.2.1]hept-1-yl)carbonyloxy]-2-oxo-1-pyrrolidinyl/acetamide on commercially obtainable, prepacked Hibar Lichrosorb RT DIOL columns (250×4 mm, granular size 10 μm) while eluting with 24% tetrahydrofuran and 0.4% isopropylamine in n-hexane.

(c) From (R)-cis-N-[2-(2,6-dimethyl-1-piperidinyl)ethyl]-2-/3-[(3-oxo-4,7,7-trimethyl-2-oxabicyclo[2.2.1]hept-1-yl)carbonyloxy]-2-oxo-1-pyrrolidinyl/acetamide there can be obtained by treatment with aqueous ammonia (R)-cis-N-[2-(2,6-dimethyl-1-piperidinyl)ethyl]-2-(3-hydroxy-2-oxo-1-pyrrolidinyl)acetamide.

M.p. 101°–102° (from ethyl acetate); [$\alpha$]$_D^{20}$ = +43°, [$\alpha$]$_{546}^{20}$ = +52°, [$\alpha$]$_{365}^{20}$ = +162° (acetonitrile, c=1.00).

(d) From (S)-cis-N-[2-(2,6-dimethyl-1-piperidinyl)ethyl]-2-/3-[(3-oxo-4,7,7-trimethyl-2-oxabicyclo[2.2.1]hept-1-yl)carbonyloxy]-2-oxo-1-pyrrolidinyl/acetamide there can be obtained by treatment with aqueous ammonia (S)-cis-N-[2-(2,6-dimethyl-1-piperidinyl)ethyl]-2-(3-hydroxy-2-oxo-1-pyrrolidinyl)acetamide.

M.p. 101°–103° (from ethyl acetate; [$\alpha$]$_D^{20}$ = −44°, [$\alpha$]$_{545}^{20}$ = −53°, [$\alpha$]$_{365}^{30}$ = −165° (acetonitrile, c=1.0).

EXAMPLE 36

Preparation of (R/S)-cis-N-[2-(2,6-dimethyl-1-piperidinyl)ethyl]-2-(3-hydroxy-2-oxo-1-pyrrolidinyl)acetamide hydrochloride 2.97 g of (R/S)-cis-N-[2-(2,6-dimethyl-1-piperidinyl)ethyl]-2-(3-hydroxy-2-oxo-1-pyrrolidinyl)acetamide are dissolved in 10 ml of ethanol. Thereto there are added 1.26 ml of a 7.9N solution of hydrogen chloride in ethanol. Thereupon, the mixture is evaporated and the residue is dried in a high vacuum. There is obtained (R/S)-cis-N-[2-(2,6-dimethyl-1-piperidinyl)ethyl]-2-(3-hydroxy-2-oxo-1-pyrrolidinyl)acetamide hydrochloride which has a decomposition point of 97°. The microanalysis shows the following values:

Empirical formula $C_{15}H_{27}N_3O_3 \cdot HCl$; m.w. 333.86. Calc.: C 53.96; H 8.45%; N 12.59%. Found: C 53.98; H 8.57%; N 12.40%.

EXAMPLE A (R/S)-cis-N-[2-(2,6-Dimethyl-1-piperidinyl)ethyl]-2-(3-hydroxy-2-oxo-1-pyrrolidinyl)acetamide can be used as the active substance for the preparation of tablets of the following composition:

| | |
|---|---|
| Active substance | 1 mg |
| Lactose | 100 mg |
| Maize starch | 68.5 mg |
| Magnesium stearate | 0.5 mg |
| | 170 mg |

The finely ground active substance, the powdered lactose and a portion of the maize starch are mixed. The mixture is sieved and then worked-up with maize starch paste. The resulting mixture is subsequently granulated, dried and sieved. The sieved granulate is mixed with magnesium stearate and the mixture is pressed to tablets weighing 170 mg and having a suitable size.

I claim:

1. A pharmaceutical composition for the control or prevention of cerebral insufficiency comprising a therapeutically effective amount of a pyrrolidine derivative of the formula

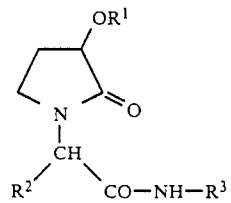

wherein $R^1$ is hydrogen or lower alkanoyl containing at most 8 carbon atoms, $R^2$ is hydrogen or lower alkyl containing at most 7 carbon atoms, and $R^3$ is hydrogen, lower alkyl containing at most 7 carbon atoms, or a group of the formula —(CH$_2$)$_n$—NR$^4$R$^5$, wherein n is a whole number of 2 to 4 and R$^4$ and R$^5$ each, independently, are hydrogen or lower alkyl containing at most 7 carbon atoms, or R$^4$ and R$^5$ taken together with the nitrogen atom are a pyrrolidinyl, piperidinyl, piperazinyl or morpholinyl group which is optionally substituted by one or two lower alkyl groups each containing at most 7 carbon atoms;
an enantiomer thereof, or a pharmaceutically acceptable acid addition salt of a compound of formula I or an enantiomer thereof which is basic, and an inert pharmaceutical carrier material.

2. A method of controlling or preventing cerebral insufficiency or improving intellectual capacity comprising administering a therapeutically effective amount of a pyrrolidine derivative of the formula

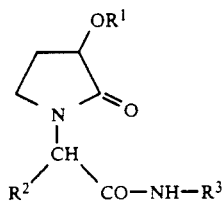

wherein R$^1$ is hydrogen or lower alkanoyl containing at most 8 carbon atoms, R$^2$ is hydrogen or lower alkyl containing at most 7 carbon atoms, and R$^3$ is hydrogen, lower alkyl containing at most 7 carbon atoms, or a group of the formula —(CH$_2$)$_n$—NR$^4$R$^5$, wherein n is a whole number of 2 to 4 and R$^4$ and R$^5$ each, independently, are hydrogen or lower alkyl containing at most 7 carbon atoms, or R$^4$ and R$^5$ taken together with the nitrogen atom are a pyrrolidinyl, piperidinyl, piperazinyl or morpholinyl group which is optionally substituted by one or two lower alkyl groups each containing at most 7 carbon atoms;
an enantiomer thereof, or a pharmaceutically acceptable acid addition salt of a compound of formula I or an enantiomer thereof which is basic.

3. A pharmaceutical composition, in accordance with claim 1, wherein the pyrrolidine derivative is (R)-cis-N-[2-(2,6-dimethyl-1-piperidinyl)ethyl]-2-(3-hydroxy-2-oxo-1-pyrrolidinyl)acetamide.

4. A pharmaceutical composition, in accordance with claim 1, wherein the pyrrolidine derivative is (R)-2-(3-hydroxy-2-oxo-1-pyrrolidinyl)acetamide.

5. A pharmaceutical composition, in accordance with claim 1, wherein the pyrrolidine derivative is (R/S)-cis-N-[2-(2,6-dimethyl-1-piperidinyl)ethyl]-2-(3-hydroxy-2-oxo-1-pyrrolidinyl)acetamide.

6. A pharmaceutical composition, in accordance with claim 1, wherein the pyrrolidine derivative is (R/S)-2-(3-hydroxy-2-oxo-1-pyrrolidinyl)acetamide.

7. A pharmaceutical composition, in accordance with claim 1, wherein the pyrrolidine derivative is (R/S)-N-[2-(diiso-propylamino)ethyl-2-(3-hydroxy-2-oxo-1-pyrrolidinyl)acetamide.

8. A method, in accordance with claim 2, wherein the pyrrolidine derivative is (R)-cis-N-[2-(2,6-dimethyl-1-piperidinyl)ethyl]-2-(3-hydroxy-2-oxo-1-pyrrolidinyl)acetamide.

9. A method, in accordance with claim 2, wherein the pyrrolidine derivative is (R)-2-(3-hydroxy-2-oxo-1-pyrrolidinyl)acetamide.

10. A method, in accordance with claim 2, wherein the pyrrolidine derivative is (R/S)-cis-N-[2-(2,6-dimethyl-1-piperidinyl)ethyl]-2-(3-hydroxy-2-oxo-1-pyrrolidinyl)acetamide.

11. A method, in accordance with claim 2, wherein the pyrrolidine derivative is (R/S)-2-(3-hydroxy-2-oxo-1-pyrrolidinyl)acetamide.

12. A method, in accordance with claim 2, wherein the pyrrolidine derivative is (R/S)-N-[2-(diisopropylamino)ethyl]-2-(3-hydroxy-2-oxo-1-pyrrolidinyl)acetamide.

* * * * *